US009545388B2

(12) United States Patent
Avantaggiati

(10) Patent No.: US 9,545,388 B2
(45) Date of Patent: Jan. 17, 2017

(54) BENZENETRICARBOXYLIC ACID AND METHODS OF USE

(71) Applicant: GEORGETOWN UNIVERSITY, Washington, DC (US)

(72) Inventor: Maria Laura Avantaggiati, Kensington, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 14/437,727

(22) PCT Filed: Oct. 22, 2013

(86) PCT No.: PCT/US2013/066073
§ 371 (c)(1),
(2) Date: Apr. 22, 2015

(87) PCT Pub. No.: WO2014/066320
PCT Pub. Date: May 1, 2014

(65) Prior Publication Data
US 2015/0238449 A1 Aug. 27, 2015

Related U.S. Application Data

(60) Provisional application No. 61/716,667, filed on Oct. 22, 2012.

(51) Int. Cl.
*A61K 31/194* (2006.01)
*A61K 45/06* (2006.01)
(52) U.S. Cl.
CPC ............. *A61K 31/194* (2013.01); *A61K 45/06* (2013.01)
(58) Field of Classification Search
None
See application file for complete search history.

(56) References Cited

U.S. PATENT DOCUMENTS

2007/0149466 A1 6/2007 Milburn et al.
2007/0259956 A1 11/2007 Thompson et al.

OTHER PUBLICATIONS

Catalina-Rodriguez et al., The mitochondrial citrate transporter, CIC, is essential for mitochondrial homeostasis, 3(10): 1220-1235 (2012).
Christofk et al., The M2 splice isoform of pyruvate kinase is important for cancer metabolism and tumour growth, Nature, 2008, 452:230-233.
Covarrubias et al., Function of reactive oxygen species during animal development: passive or active?, Dev Biol., 2008, 320:1-11.
Czarnecka et al., Mitochondrial DNA mutations in cancer-from bench to bedside, Front Biosci, 2010, 15:37-60.
Desmedt et al., Strong time dependence of the 76-gene prognostic signature for node-negative breast cancer patients in the TRANSBIG multicenter independent validation series, Clin Cancer Res., 2007, 13:3207-14.
El Mjiyad et al., Sugar-free approaches to cancer cell killing, Oncogene, 2011, 30:253-264.
Fontana et al., Extending healthy life span—from yeast to humans, Science, 2010, 325:321-326.
Friedman et al., Cleft palate, retrognathia and congenital heart disease in velo-cardio-facial syndrome: a phenotype correlation study, Int J Pediatr Otorhinolaryngol., 2011, 75:1167-1172.
Fulda et al., Targeting mitochondria for cancer therapy, Nat Rev Drug Discov., 2010, 9:447-464.
Gargini et al., Therapy mediated by mitophagy abrogates tumor progression, Autophagy, 2011, 7:466-76.
Green , Mitochondria and the autophagy-inflammation-cell death axis in organismal aging, Science, 2011, 333:1109-1112.
Guido et al., Mitochondrial fission induces glycolytic reprogramming in cancer-associated myofibroblasts, driving stromal lactate production, and early tumor growth, Oncotarget, 2012, 3:798-810.
Guppy et al., The role of the Crabtree effect and an endogenous fuel in the energy metabolism of resting and proliferating thymocytes, Eur J Biochem, 1993, 212:95-99.
Hatzivassiliou et al., ATP citrate lyase inhibition can surppress tumor cell growth, Cancer Cell, 2005, 8:311-321.
Infantino et al., Transcription of the mitochondrial citrate carrier gene: role of SREBP-1, upregulation by insuin and downregulation by PUFA, Biochem Biophys Res Commun, 2007, 356: pp. 249-254.
Infantino et al., The mitochondrial citrate carrier: a new player in inflammation, Biochem J., 2011, 438: 433-436.
Ivshina et al., Gentic reclassification of histologic grade delineates new clinical subtypes of breast cancer, Cancer Res, 2006, 66:10292-10301.
Joseph et al., The mitochondrial citrate/isocitrate carrier plays a regulatory role in glucose-stimulated insulin secretion, J Biol Chem., 2006, 281:35624-35632.
Kang et al., Regulation of tumor cell mitochondrial homeostasis by an organelle-specific Hsp90 chaperone network, Cell., 2007, 131:257-270.
Kaplan et al., Functional levels of mitochondrial anion transport proteins in non-insulin-dependent diabetes mellitus, Mol Cel Biochem, 1991, 107: 79-86.
Kaplan et al., Kinetic characteristics of citrate influx and efflux with mitochondria from Morris hepatomas 3924A and 16, Cancer Res, 1982, 42:4399-4407.
Kho et al., Conserved mechanisms across development and tumorigenesis revealed by a mouse development perspective of human cancers, Genes Dev., 2004, 18:629-640.
Kolukula et al., SLC25A1, or CIC, is a novel transcriptional target of mutant p53 and a negative tumor prognostic marker, Oncotarget, 5(5):1212-1225 (2014).
Koppeno et al., Otto Warburg's contributions to current concepts of cancer metabolism, Nat Rev Cancer, 2011, 11:325-337.
Lee et al., Disease-causing mutations in parkin impair mitochondrial ubiquitination, aggregation, and HDAC6-dependent mitophagy, J Cell Biol., 2010, 189:671-689.

(Continued)

*Primary Examiner* — Samantha Shterengarts
(74) *Attorney, Agent, or Firm* — Kilpatrick Townsend & Stockton, LLP

(57) ABSTRACT

Methods of treating or preventing cancer and/or a neurodegenerative disorder in a subject are provided. The methods comprise administering to a subject a therapeutically effective amount of 1,2,3-benzenetricarboxylic acid or a hydrate or pharmaceutically acceptable salt thereof.

3 Claims, 11 Drawing Sheets

(56) References Cited

OTHER PUBLICATIONS

Lisanti et al., Understanding the "lethal" drivers of tumor-stroma co-evolution: emerging role(s) for hypoxia, oxidative stress and autophagy/mitophagy in the tumor micro-environment, Cancer Biology & Therapy, 10:6, 537-542, Sep. 15, 2010.
Lisanti et al., Hydrogen peroxide fuels aging, inflammation, cancer metabolism and metastasis: the seed and soil also needs "fertilizer", Cell Cycle, 2011, 10:2440-2449.
Ma et al., Identification of the substrate binding sites within the yeast mitochondrial citrate transport protein, J Biol Chem, 2007, 282:17210-17220.
Ma et al., The yeast mitochondrial citrate transport protein: characterization of transmembrane domain III residue involvement in substrate translocation, J Biol Chem, 2005, 280:2331-2340.
Maftah et al., 10-N nonyl-acridine orange: a fluorescent probe which stains mitochondria independently of their energetic state, Biochem Biophys Res Commun., 1989, 164, 99. 185-190.
Martinez-Outschoorn et al., The autophagic tumor stroma model of cancer or "battery-operated tumor growth", Cell Cycle, 9:21, 4297-4306, Nov. 1, 2010.
Martinez-Outschoorn et al., Power Surge: Supporting Cells "Fuel" Cancer Cell Mitochondria, Cell Metab., 2012, 15: 4-5.
Meechan et al., Three phases of DiGeorge/22q11 deletion syndrome pathogenesis during brain development: patterning, proliferation, and mitochondrial functions of 22q11 genes, Int J Dev Neurosci, 2011, 29:283-294.
Metallo et al., Reductive glutamine metabolism by IDH1 mediates lipogenesis under hypoxia, Nature, 2011, 481:380-384.
Mullen et al., Reductive carboxylation supports growth in tumour cells with defective mitochondria, Nature, 2011, 481:385-388.
Newsholme , Effect of citrate on the activities of 6-phosphofructokinase from nervous and muscle tissues from different animals and its relationships to the regulation of glycolysis, Biochem J., 1977, 166:123-129.
Nicholls , Mitochondrial ion circuits. Essays Biochem, Essays Biochem, 2010, 47:25-35.
Odgren et al., Molecular characterization of mitofilin (HMP), a mitochondria-aasociated protein with predicted coiled coil and intermembrane space targeting domains, J Cell Sci., 1996, 109:2253-2264.

Owen et al., The key role of anaplerosis and cataplerosis for citric acid cycle function, J Biol Chem, 2002, 277:30409-30412.
Palmieri , Diseases caused by defects of mitochondrial carriers: a review, Biochim Biophys Acta, 2008, 1777:564-578.
Palmieri et al., Mitochondrial metabolite transport, Essays Biochem, 2010, 16 pages.
International Patent Application No. PCT/US2013/066073 , International Search Report and Written Opinion, mailed Jan. 16, 2014, 9 pages.
International Patent Application No. PCT/US2013/066073 , International Preliminary Report on Patentability, mailed May 7, 2015, 6 pages.
Plun-Favreau et al., Cancer and neurodegeneration: between the devil and the deep blue sea, PLoS Genet., 2010, 6(12):e1001257.
Raj et al., Selective killing of cancer cells by a small molecule targeting the stress response to ROS, Nature, 2011, 475:231-234.
Rhodes et al., Genes, Pathways, and Networks in a Collection of 18,000 Cancer Gene Expression Profiles, Neoplasia, 2007, 9:166-180.
Rogina et al., Extended life-span conferred by cotransporter gene mutations in *Drosophila*, Science, 2000, 290:2137-2140.
Rossignol et al., Energy substrate modulates mitochondrial structure and oxidative capacity in cancer cells, Cancer Res, 2004, pp. 985-993.
Stoffel et al., The human mitochondrial citrate transporter gene (SLC20A3) maps to chromosome band 22q11 within a region implicated in DiGeorge syndrome, velo-cardiofacial syndrome and schizophrenia, Hum Genet, 1996, 98:113-115.
Sun et al., Mitochondrial and Plasma Membrane Citrate Transporters: Discovery of Selective Inhibtors and Application to Structure/Function Analysis, Mol Cel Pharmacol, 2010, 2:101-110.
Trachootham et al., Selective killing of oncogenically transformed cells through a ROS-mediated mechanism by beta-phenylethyl isothiocyanate, Cancer Cell, 2006, 10:241-252.
Valentin-Vega et al., Mitochondrial dysfunction in ataxia telangiectasia, Blood, 2011, 119:1490-500.
Wang et al., Mitochondria removal by autophagy, Autophagy, 2011, 7:297-300.
Weigel et al., Transcriptional control of estrogen receptor in estrogen receptor-negative breast carcinoma, Cancer Res, 1993, 53:3472-3474.
Yen et al., How to live long and prosper: autophagy, mitochondria and aging, Physiology, 2008, 23:248-265.

C Correlation between clinical outcome and high CIC levels

| Study | Survival<br>Ishvinia et al.<br>(2006) | Metastatic disease | |
|---|---|---|---|
| | | Study | Desmedt et al.<br>(2007) |
| N= | 69 vs 158 | N= | 18 vs 6 |
| p-value | <0.0001 | p-value | 0.002 |

BENZENETRICARBOXYLIC ACID AND METHODS OF USE

CROSS-REFERENCE TO PRIORITY APPLICATION

This application claims priority to U.S. Provisional Application No. 61/716,667, filed Oct. 22, 2012, which is incorporated herein by reference in its entirety.

BACKGROUND

Disregulation of the pathways that preserve mitochondrial integrity hallmarks many human diseases including diabetes, neurodegeneration, aging, and cancer. The mitochondrial citrate transporter gene, SLC25A1 or CIC, maps on chromosome 22q11.21, a region amplified in some tumors and deleted in developmental disorders known as velo-cardio-facial and DiGeorge syndromes. Several chromosomal translocations and amplifications involving 22q11.2 have been described in various tumors, while microdeletions of this region give rise to developmental disorders known as velo-cardio-facial (VCFS) and DiGeorge syndromes (DGS) as well as to some forms of schizophrenia.

SUMMARY

Provided herein are methods for the use of benzenetricarboxylic acid for treating or preventing cancer and neurodegenerative disorders. The method of treating or preventing cancer in a subject comprises administering to the subject an effective amount of a compound of the following structure:

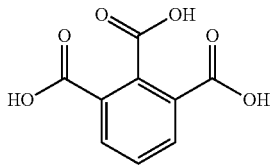 [SMILES: O=C(O)c1cccc(C(=O)O)c1C(=O)O]

or a hydrate or pharmaceutically acceptable salt thereof. The method can further comprise administering a second therapeutic agent to the subject. Optionally, the second therapeutic agent is a chemotherapeutic agent. Optionally, the cancer is breast cancer, lung cancer, or bladder cancer.

A method of treating or preventing a neurodegenerative disorder in a subject comprises administering to the subject an effective amount of a compound of the following structure:

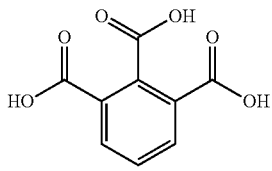 [SMILES: O=C(O)c1cccc(C(=O)O)c1C(=O)O]

or a hydrate or pharmaceutically acceptable salt thereof. Optionally, the neurodegenerative disorder is Parkinson's disease. The method can further comprise administering a second therapeutic agent to the subject. Optionally, the second therapeutic agent is selected from the group consisting of levadopa, a dopamine agonist, an anticholinergic agent, a monoamine oxidase inhibitor, a COMT inhibitor, amantadine, rivastigmine, an NMDA antagonist, a cholinesterase inhibitor, riluzole, an anti-psychotic agent, an anti-depressant, and tetrabenazine. The details of one or more embodiments are set forth in the drawings and the description below. Other features, objects, and advantages will be apparent from the description and drawings, and from the claims.

mice are shown. Bars represent standard deviations; asterisk (*) represents p-value<0.05 and double-asterisk (**) represents p-value<0.01.

Figure 4:
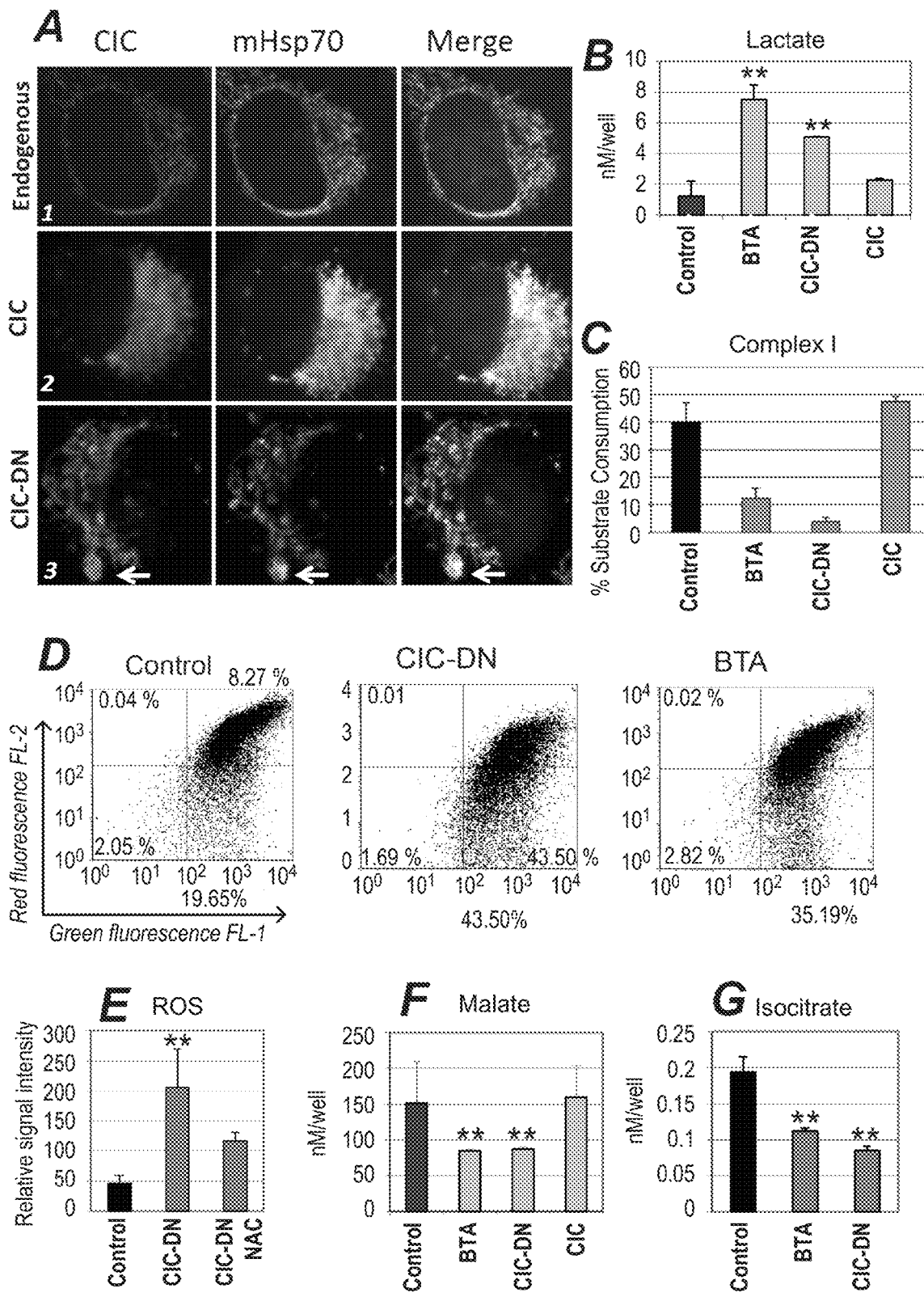

FIG. 4 shows mitochondrial and metabolic effects arising from CIC inhibition. Panel A shows H1299 cells (panel set indicated as 1) or cells expressing CIC (2) or CIC-DN (3) stained with anti-CIC (red) or anti-mitochondrial Hsp70 (mHsp70, green) antibodies, and counterstained with DAPI. The DAPI signal is shown only in the merged images. For these experiments, cells were harvested 46 hours after tetracycline induction. The arrow in panel A3 indicates mitochondria with enlarged and abnormal morphology (mega-mitochondria). The next set of panels shows measurements of lactate levels (B) and of complex I (C); of mitochondrial membrane potential assessed with a JC1 assay (MMP) (D); of ROS (E); of malate (F); and of isocitrate (G) levels. Measurements were performed in cells treated with DMSO (indicated as control) or with BTA, or expressing CIC or CIC-DN at 16 hours after treatment or tetracycline induction, respectively. In the case of ROS levels, panel D shows a dot plot or red (FL-2) versus green fluorescence (FL-1) of JC1 staining. In mitochondria with intact membrane potential the JC1 dye concentrates into red fluorescent aggregates, while depolarized mitochondria are unable to concentrate the JC1 and exhibit green fluorescence. The percentage of cells with depolarized mitochondrial membrane is shown in bold at the bottom of each panel.

Figure 5:
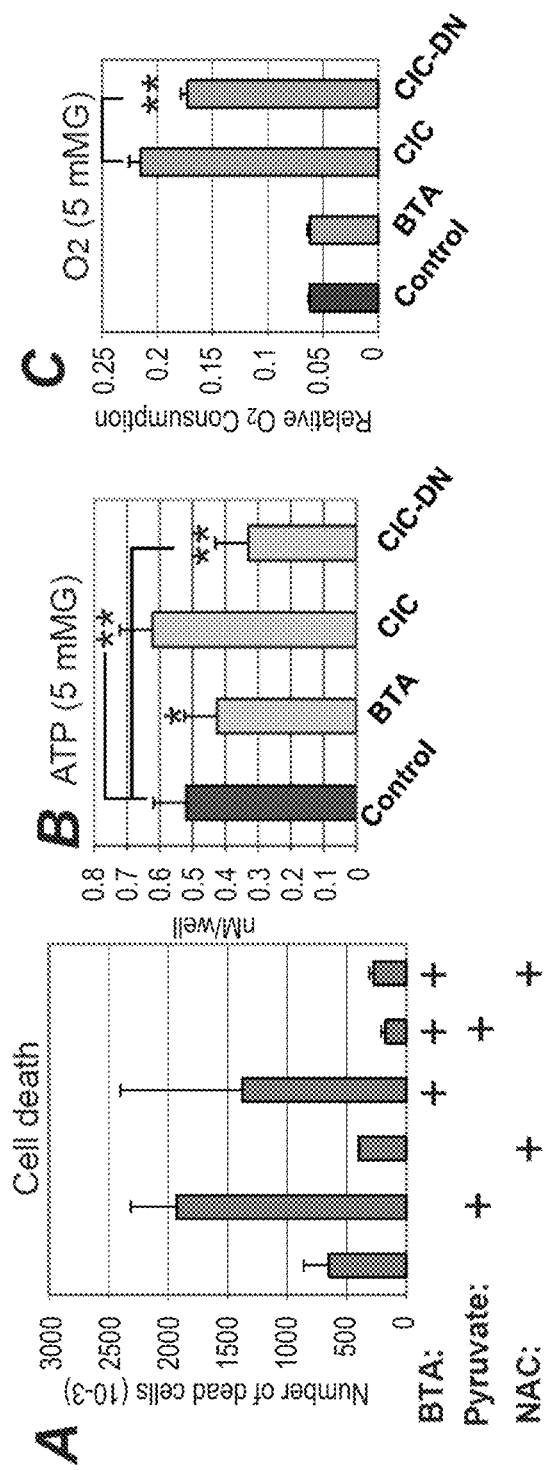
Figure 5:
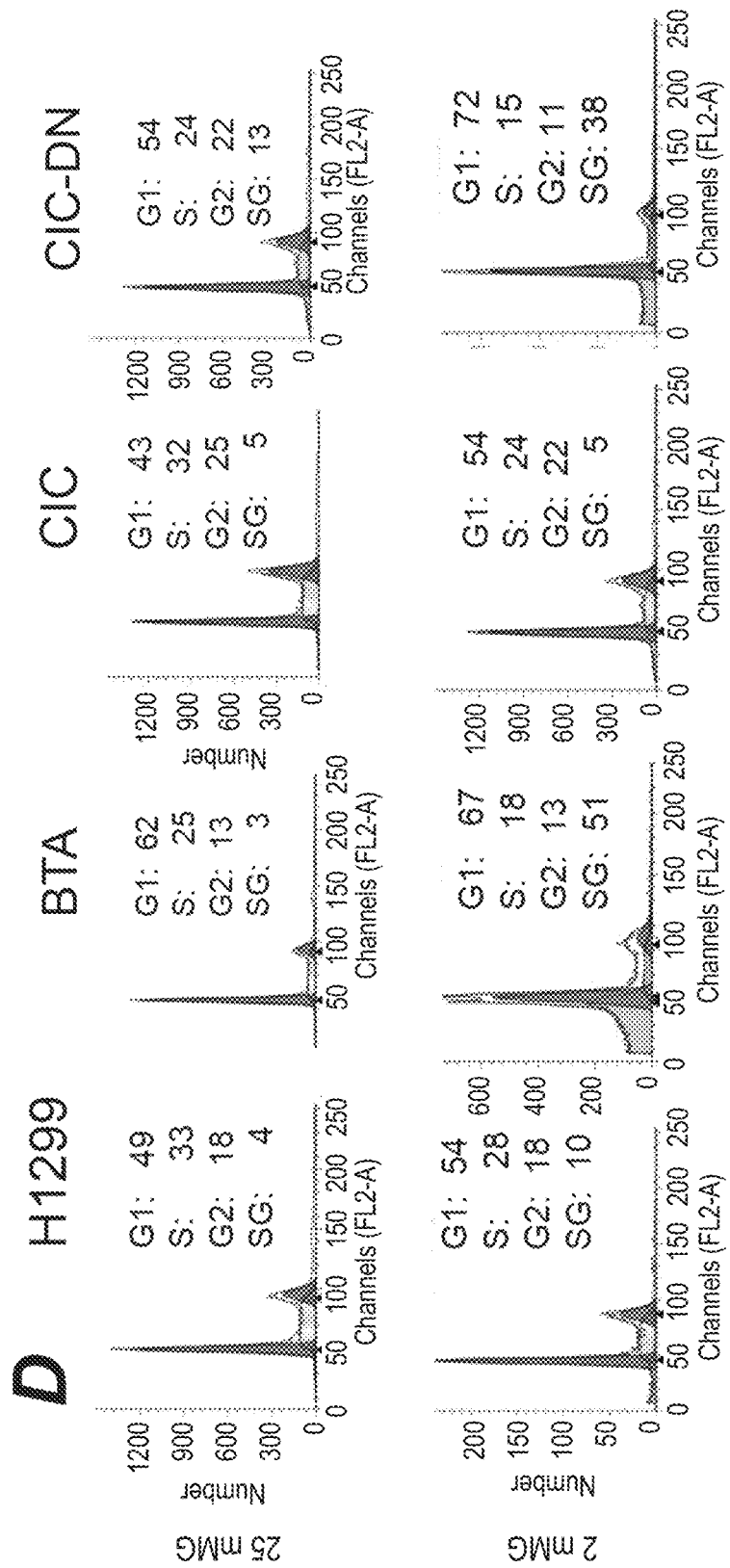
Figure 5:
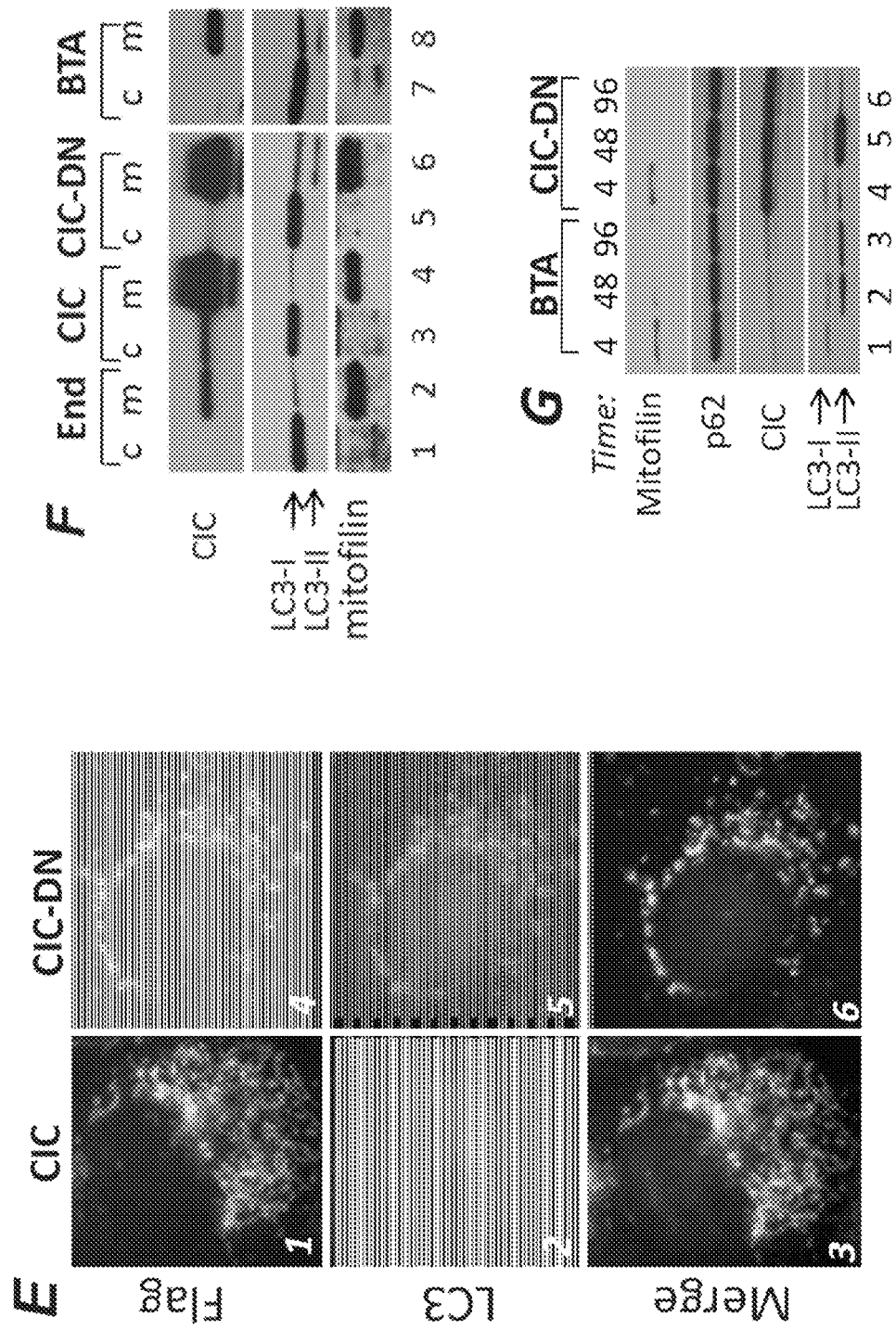

FIG. 5 shows that inhibition of CIC hampers survival during metabolic stress and induces mitochondrial loss via autophagy. Panel A shows cell death assessed with trypan blue exclusion in cells treated with DMSO or with BTA, in the presence or absence of 5 mM methyl-pyruvate or 2 mM NAC. ATP (Panel B) and Oxygen consumption levels (Panel C) in cells cultured in 5 mM glucose and mock treated (DMSO, Control) or treated with BTA, or in cells expressing CIC or CIC-DN, 16 hours after treatments. Panel D shows cell cycle profiles of control H1299 cells, or of cells treated with 1 mM BTA, or expressing the indicated CIC proteins, cultured in either 25 mM (upper panels) or in 2 mM Glucose (bottom panels). The percentages of cells distributed in the G1-, S-, or G2-phases of the cells cycle are shown. Apoptotic cells are identified as the Sub-G1 (SG) population. Panel E shows immuno-fluorescence experiments similar to those described in FIG. 4A performed in cells expressing epitope tagged Flag-CIC (panels 1 to 3) or Flag-CIC-DN (panels 3 to 6) proteins. Cells were stained with anti-Flag (green, panels 1 and 4) and anti-LC3 (red, panels 2 and 5) antibodies, and counterstained with DAPI. Merged images are shown in panels 3 and 6. The results of these immuno-fluorescence experiments were confirmed with cellular sub-fractionation experiments shown in Panel F. Cytoplasmic (c) and mitochondrial (m) fractions derived from naïve 293T cells (lanes 1,2) or 293T cells expressing CIC (lanes 3,4) or CIC-DN (lanes 5,6) or treated with BTA (lanes 7,8), were probed with anti-CIC, anti-LC3, or anti-mitofilin antibodies, as indicated. The two arrows in the LC3 blot indicate cytosolic (-I) or activated (-II) LC3 forms. An enrichment of LC3-II in the mitochondria of cells expressing CIC-DN or BTA is shown in lanes 6 and 8, respectively. All images shown were derived from the same autoradiogram at identical times of exposures, but lanes in between samples of interest were eliminated. Panel G shows the time course (in hours, indicated at the top of each panel) of BTA-treated (lanes 1 to 3) or CIC-DN induced cells (lanes 4 to 6). The anti-mitofilin, anti-p62 (employed as a general autophagic marker), anti-CIC, or anti LC3 specific immuno-blots are shown.

Figure 6:
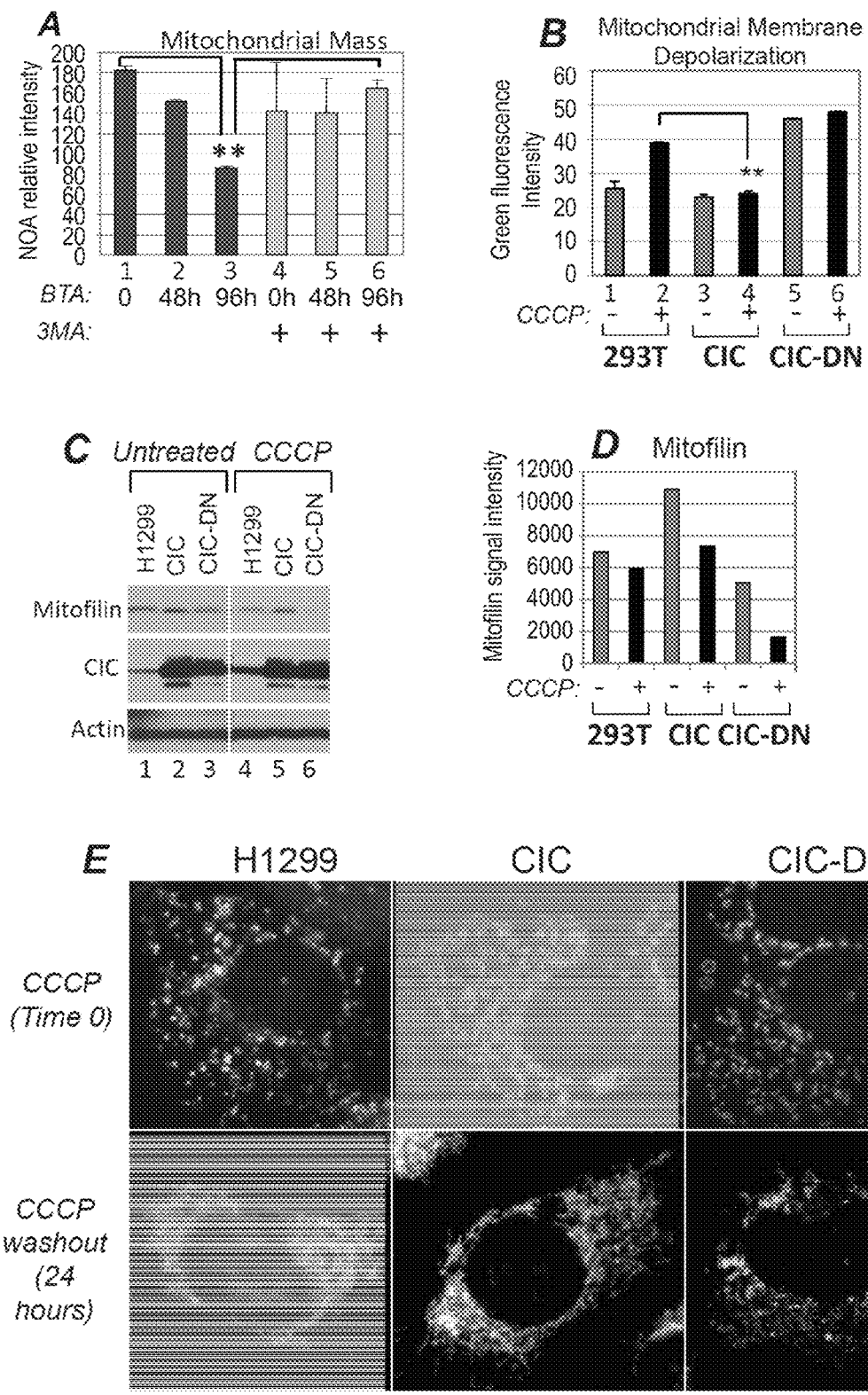

FIG. 6 shows that CIC protects from mitochondrial damage and depletion following respiration injury. Panel A provides an assessment with NOA staining of mitochondrial mass as a function of time (in hours) in control cells (lanes 1 and 4), or in cells treated with BTA (lanes 2-3 and 5-6) and in the absence (lanes 1-to-3) or presence (lanes 4-to-6) of 5 mM 3MA. Double asterisks refer to p<0.05. Brackets refer to the comparison of values expressed in 3 versus 1, or 3 versus 6. Panel B shows the measurement of mitochondrial membrane depolarization with the JC1 assay in the absence (−, lanes 1,3,5) or presence (+, lanes 2,4,6) of 20 micro-M CCCP in the cell lines indicated at the bottom of each panel. The diagram shows histograms of JC1 green fluorescence intensity, indicative of depolarization, derived from a duplicate experiment. Panel C shows the H1299 cell lines indicated at the bottom of each panel were left untreated (lanes 1-3) or treated with CCCP (20 micro-M, lanes 4-6) for 16 hours, at which time CCCP was removed from the media. Cells were replenished with fresh media, incubation was carried out for additional 2 hours, after which time cell extracts were probed with the antibodies indicated at the side of each panel. The endogenous CIC levels increased in CCCP treated versus untreated cells (lane 4 versus lane 1, respectively). The image shown is derived from the same autoradiogram where lanes between the samples of interest were cropped. Panel D shows a quantification of the mitofilin signal. Panel E shows the immuno-fluorescence of H1299 cells treated with CCCP for four hours (indicated as time 0, upper panels), or after 24 hours of CCCP wash-out. All panels in this Figure show the merged signals derived from the anti-CIC (red) and anti-Hsp70 (green) staining. Approximately 70% of cells expressing CIC-DN showed the disrupted mitochondrial network even after 24 hours of recovery from CCCP, compared to control H1299 or CIC-expressing cells that displayed this phenotype in less 10% of cells.

Figure 7:
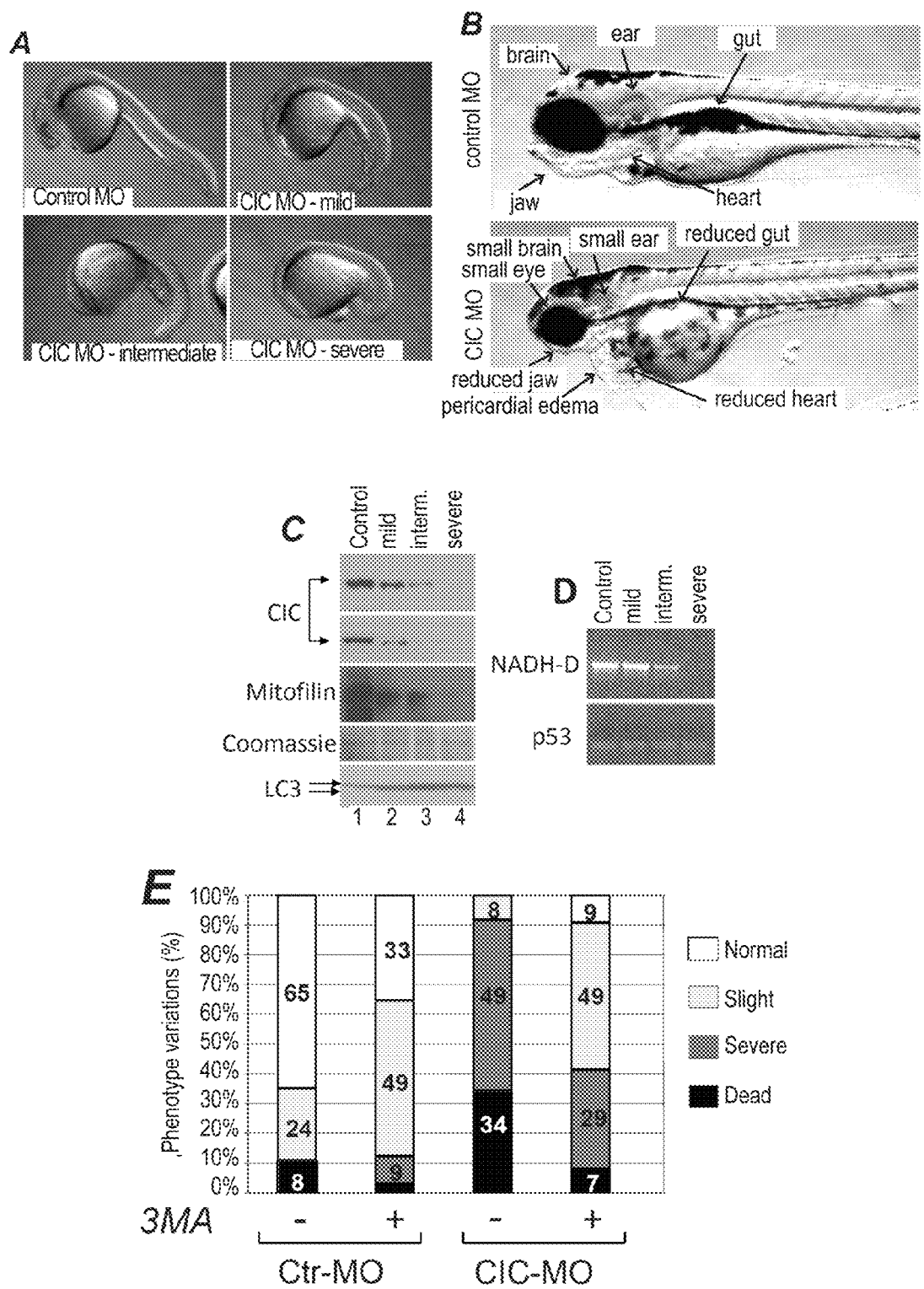

FIG. 7 shows that the knock-down of CIC in zebrafish results in mitochondrial DNA depletion and activation of autophagy. Panel A shows Zebrafish embryos injected with control morpholino (Control MO) or with three different doses of the CIC specific morpholino (CIC MO), resulting in a progressively abnormal phenotypes classified from mild to severe. Panel B shows phenotypes of zebrafish injected with control or CIC MO at 4 days post-development. Images were captured at identical magnification. Panel C shows immuno-blot of pools of 15-30 embryos of each phenotype shown in Panel A, with antibodies listed at the side of each panel. Two different exposures of the CIC-specific immuno-blot are shown. In zebrafish extracts the two main LC3 forms, I and II, could be detected and are indicated by arrows. Panel D shows DNA extracted from pooled embryos representative of each phenotype was probed in semi-quantitative PCR by using primers that amplify either 1 Kb of mtDNA encompassing the mitochondrial gene NADH-dehydrogenase (NADH-D; top panel), or the nuclear p53 gene (bottom panel). Panel E shows the survival of embryos injected with control MO or with CIC-MO grown in media containing (+) or lacking (−) 5 mM 3MA. The percentages of each phenotype classified as normal, slight, severe, and dead are indicated by bars of different shades.

Figure 8:
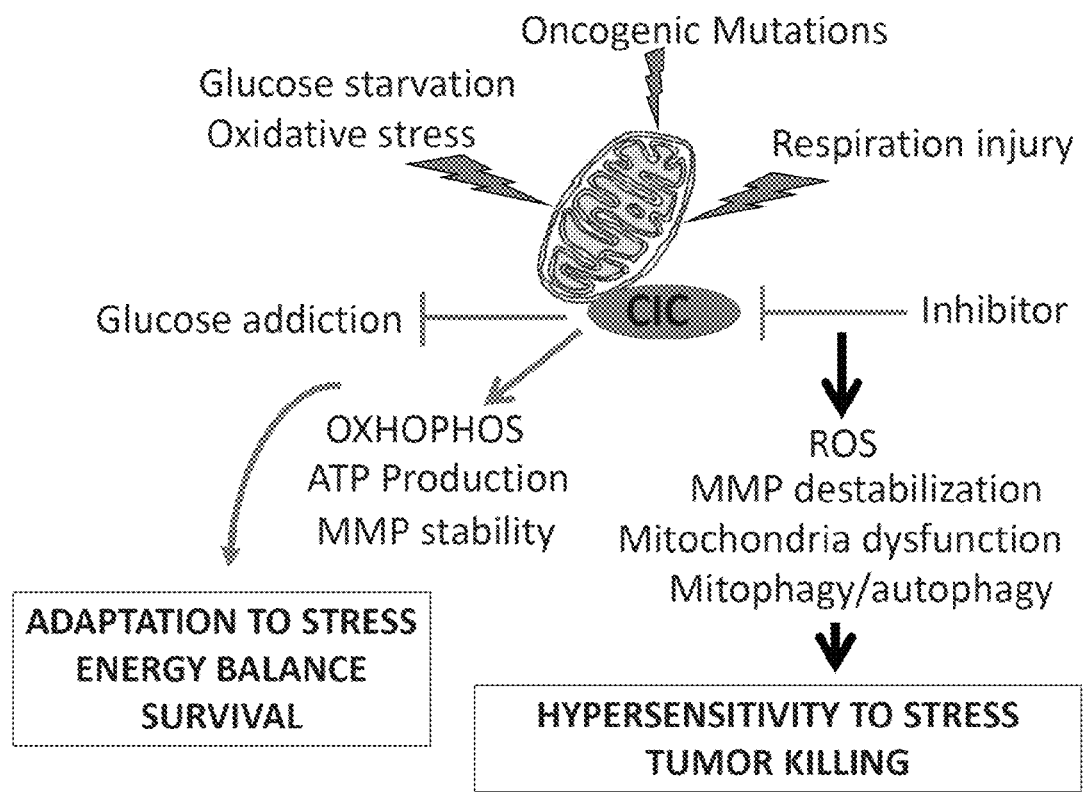

FIG. 8 depicts a summary of the finding that CIC maintains mitochondrial homeostasis in tumor cells.

DETAILED DESCRIPTION

Described herein are methods for treating and preventing cancer and/or neurodegenerative disorders in a subject. The methods of treating or preventing cancer or a neurodegenerative disorder in a subject includes administering to the subject a benzenetricarboxylic acid (e.g., 1,2,3-benzenetricarboxylic acid hydrate). The benzenetricarboxylic acid is administered in an effective amount to prevent or treat one or more symptoms of cancer or neurodegenerative disorders.

I. Compounds

A benzenetricarboxylic acid useful in the methods described herein comprises 1,2,3-benzenetricarboxylic acid, as represented by Compound I:

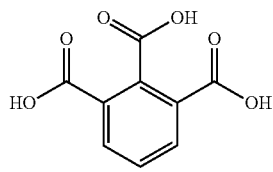

I or a hydrate or pharmaceutically acceptable salt thereof.

Optionally, the 1,2,3-benzenetricarboxlic acid is a hydrate as represented by Compound I-A:

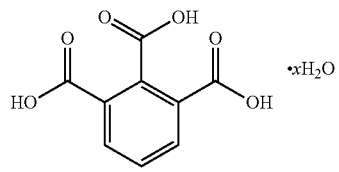

I-A

In Compound I-A, x is an integer from 1 to 20.

II. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught therein.) Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

III. Methods of Making the Compounds

The compounds described herein can be prepared in a variety of ways known to one skilled in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Compound I include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety. The synthesis and subsequent testing of various compounds as described by Compound I to determine efficacy is contemplated.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Optionally, the compounds described herein can be obtained from commercial sources. The compounds can be obtained from, for example, Sigma-Aldrich (St. Louis, Mo.).

IV. Methods of Use

Provided herein are methods to treat, prevent, or ameliorate cancer or neurodegenerative disorders in a subject. The methods include administering to a subject an effective amount of one or more of the compounds or compositions described herein, or a hydrate or pharmaceutically acceptable salt thereof. The method can include selecting a subject with cancer or a neurodegenerative disease, using methods within the art. The expression "effective amount," when used to describe an amount of compound in a method, refers to the amount of a compound that achieves the desired pharmacological effect or other effect, for example, an amount that results in tumor growth rate reduction. The compounds and compositions described herein or pharmaceutically acceptable salts thereof are useful for treating cancer and neurodegenerative disorders in humans, including, without limitation, pediatric and geriatric populations, and in animals, e.g., veterinary applications.

Optionally, the cancer is breast cancer, lung cancer, or bladder cancer. Optionally, the cancer is brain cancer, colorectal cancer, cervical cancer, gastrointestinal cancer, genitourinary cancer, head and neck cancer, ovarian cancer, pancreatic cancer, prostate cancer, renal cancer, skin cancer, or testicular cancer.

Optionally, the neurodegenerative disorder is Parkinson's disease. Optionally, the neurodegenerative disorder is Alexander disease, Alper's disease, Alzheimer disease, amyotrophic lateral sclerosis, ataxia telangiectasia, Batten disease (also known as Spielmeyer-Vogt-Sjogren-Batten disease), Canavan disease, Cockayne syndrome, Corticobasal degeneration, Creutzfeldt-Jakob disease, Huntington disease, Kennedy's disease, Krabbe disease, Lewy body dementia, Machado-Joseph disease, Spinocerebellar ataxia type 3, multiple sclerosis, multiple system atrophy, Pelizaeus-Merzbacher disease, Pick's disease, Primary lateral sclerosis, Refsum's disease, Sandhoff disease, Schilder's disease, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tay-Sachs, Transmissible spongiform encephalopathies (TSE), and Tabes dorsalis.

The method of treating or preventing cancer and neurodegenerative disorders in a subject can further comprise administering to the subject a therapeutic agent or radiation therapy or a combination thereof. Thus, the provided compositions and methods can include one or more additional agents. The one or more additional agents and the compounds described herein or pharmaceutically acceptable salts or prodrugs thereof can be administered in any order, including concomitant, simultaneous, or sequential administration. Sequential administration can be temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Therapeutic agents include, but are not limited to, chemotherapeutic agents. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, bexarotene, gefitinib, erlotinib, gemcitabine, paclitaxel, docetaxel, topotecan, irinotecan, temozolomide, carmustine, vinorelbine, capecitabine, leucovorin, oxaliplatin, bevacizumab, cetuximab, panitumumab, bortezomib, oblimersen, hexamethylmelamine, ifosfamide, CPT-11, deflunomide, cycloheximide, dicarbazine, asparaginase, mitotant, vinblastine sulfate, carboplatin, colchicine, etoposide, melphalan, 6-mercaptopurine, teniposide, vinblastine, antibiotic derivatives (e.g. anthracyclines such as doxorubicin, liposomal doxorubicin, and diethylstilbestrol doxorubicin, bleomycin, daunorubicin, and dactinomycin); antiestrogens (e.g., tamoxifen); antimetabolites (e.g., fluorouracil (FU), 5-FU, methotrexate, floxuridine, interferon alpha-2B, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cisplatin, vincristine and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chlorambucil, mechlorethamine (nitrogen mustard) and thiotepa); and steroids (e.g., bethamethasone sodium phosphate).

Therapeutic agents further include, but are not limited to, levadopa, a dopamine agonist, an anticholinergic agent, a monoamine oxidase inhibitor, a COMT inhibitor, amantadine, rivastigmine, an NMDA antagonist, a cholinesterase inhibitor, riluzole, an anti-psychotic agent, an antidepressant, and tetrabenazine.

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of cancer or a neurodegenerative disorder), during early onset (e.g., upon initial signs and symptoms of cancer or a neurodegenerative disorder), or after the development of cancer or a neurodegenerative disorder. Prophylactic administration can occur for several days to years prior to the manifestation of symptoms of cancer or a neurodegenerative disorder. Therapeutic treatment involves administering to a subject a therapeutically effective amount of the compounds and compositions or pharmaceutically acceptable salts thereof as described herein after cancer or a neurodegenerative disorder is diagnosed.

V. Kits

Also provided herein are kits for treating or preventing cancer or a neurologic disorder in a subject. A kit can include any of the compounds or compositions described herein. For example, a kit can include Compound I. A kit can further include one or more additional agents, such as a chemotherapeutic agent (e.g., gemcitabine, paclitaxel, or tamoxifen), levadopa, a dopamine agonist, an anticholinergic agent, a monoamine oxidase inhibitor, a COMT inhibitor, amantadine, rivastigmine, an NMDA antagonist, a cholinesterase inhibitor, riluzole, an anti-psychotic agent, an anti-depressant, and/or tetrabenazine. A kit can include an oral formulation of any of the compounds or compositions described herein. A kit can additionally include directions for use of the kit (e.g., instructions for treating a subject), a container, a means for administering the compounds or compositions, and/or a carrier.

As used herein the terms treatment, treat, or treating refer to a method of reducing or delaying the progression of one or more symptoms of a disease or condition in a subject with cancer or a neurodegenerative disorder. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating cancer is considered to be a treatment if there is a 10% reduction in one or more symptoms or signs (e.g., size of the tumor or rate of tumor growth) of the disease in a subject as compared to a control. As used herein, control refers to the untreated condition (e.g., the tumor cells not treated with the compounds and compositions described herein). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder. For example, the method is considered to be a prevention of a neurodegenerative disorder if there is a reduction or delay in onset, incidence, severity, or recurrence of neurodegeneration, or one or more symptoms of neurodegeneration (e.g., tremor, weakness, memory loss, rigidity, spasticity, atrophy, dementia) in a subject susceptible to neurodegeneration compared to control subjects susceptible to neurodegeneration that did not receive a compound as described herein. The reduction or delay in onset, incidence, severity, or recurrence of neurodegeneration can be a 10%, 20%, 30%, 40%, 50%, 60%, 70%, 80%, 90%, 100%, or any percent reduction in between 10% and 100% as compared to native or control levels.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

Example 1

Figure 1:
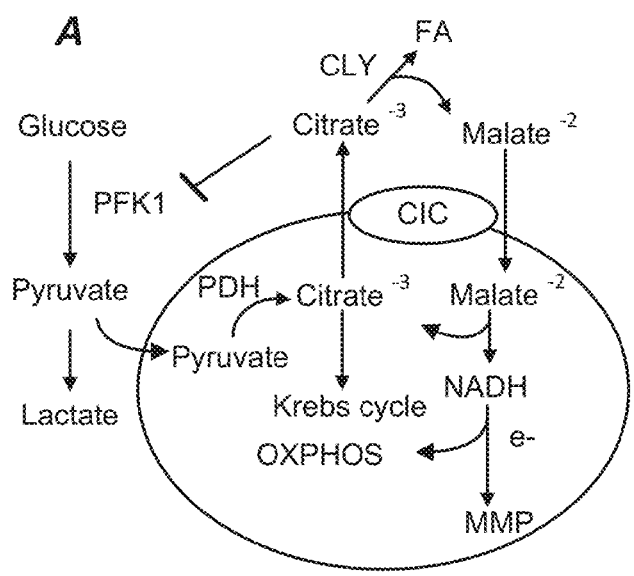
FIG. 1 shows that CIC is involved in tumor proliferation. Panel A depicts the role of CIC in metabolism. Panel B shows the CIC mRNA expression levels in human normal or breast tumor tissues. Panel C shows the negative correlation between CIC expression levels and the development of metastatic disease in breast cancer. Panel D shows CIC expression levels in the breast cancer cell lines indicated at the top of each panel. Panels E and F show clonogenic assays performed in MBA-MD-231 cells. Representative CIC expression levels relative to actin levels are shown in panel E (bottom panel), and representative plates derived from the combination transfection experiments are shown at the bottom of panel F. Panel G shows Mitochondrial (m) and cytoplasmic (c) fractions derived from 293T cells transfected with the pcDNA4/TO control vector, or expressing CIC or CIC-DN. The expression levels of CIC and COX IV, used as a mitochondrial marker, are shown.
Figure 1:
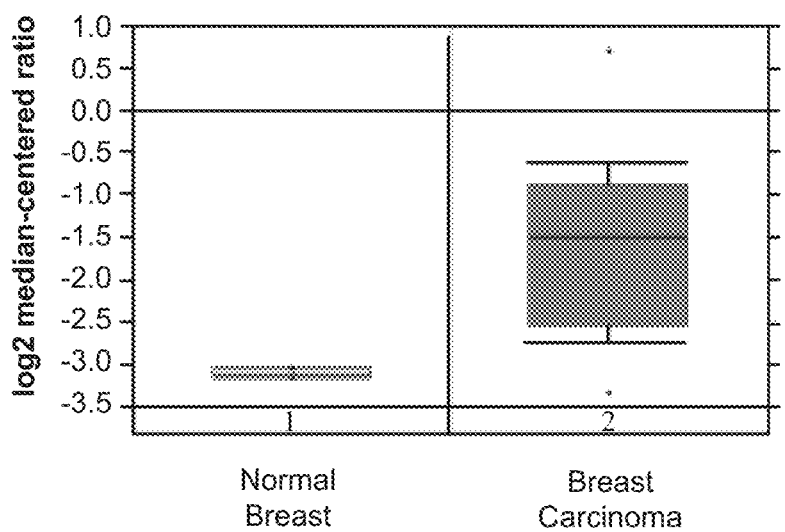
Figure 1:
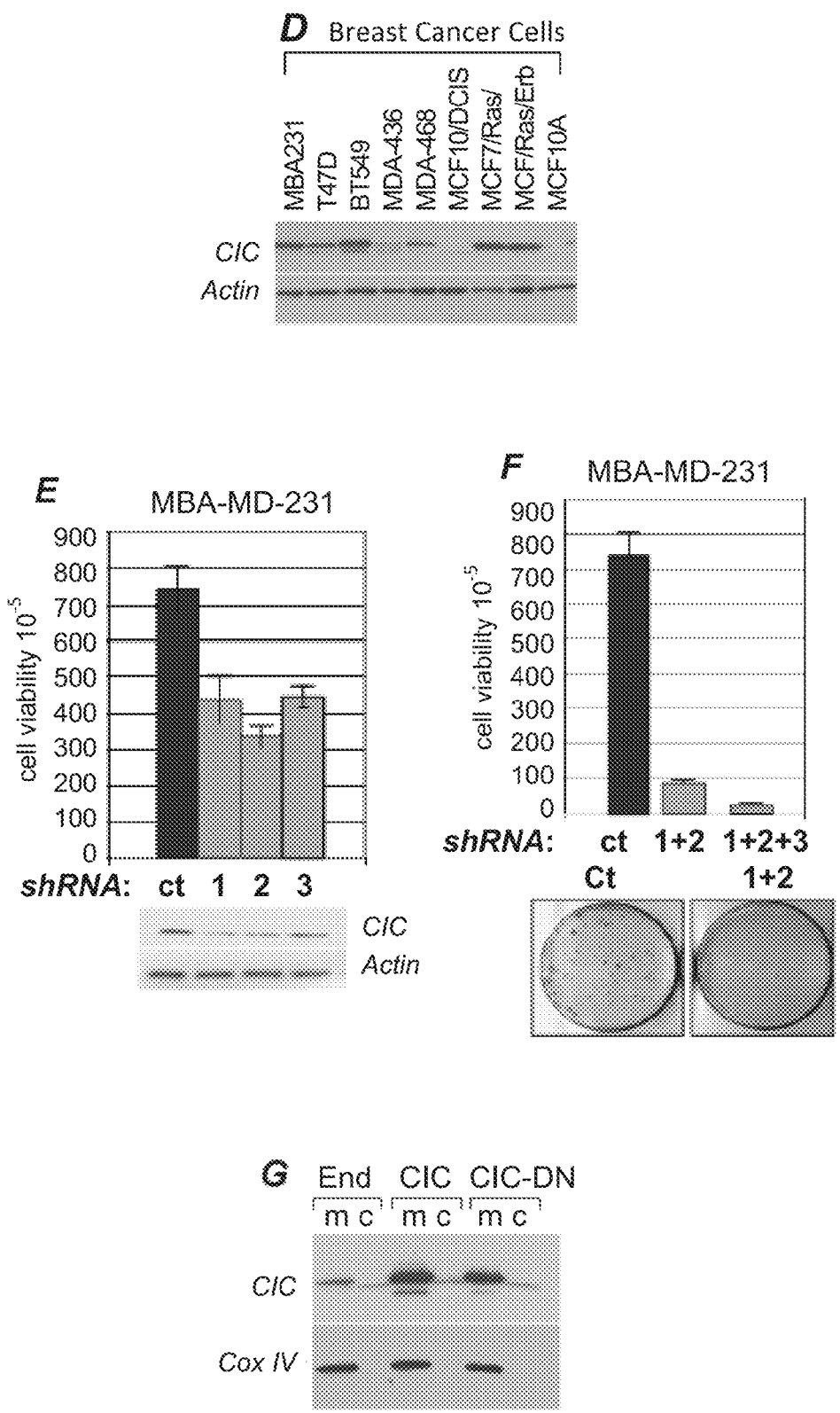

Mechanistically, CIC promotes the efflux across the mitochondria of tricarboxylic citrate in exchange for dicarboxylic cytosolic malate (the citrate malate antiport), leading to important metabolic adjustments (see FIG. 1A). As shown in FIG. 1A, CIC catalyzes the electroneutral exchange across the inner mitochondrial membrane of the tricarboxylate citrate plus a proton for the dicarboxylate malate. Once in the cytoplasm citrate is cleaved by citrate lyase (CLY), providing a source for fatty acids (FA) synthesis and producing malate that is imported in the mitochondria. Here, malate oxidation generates NADH, which donates its electrons to the transport chain thereby maintaining oxidative phosphorylation (OXHOPHOS) and mitochondrial membrane potential (MMP). Cytoplasmic citrate can also act as an allosteric inhibitor of Phosphofructokinase-1 (PK1), a key glycolytic enzyme. Glycolysis in the cytoplasm generates a second key substrate, pyruvate that is either converted into lactate to produce ATP in an anaerobic reaction, or it is transported into the mitochondria, converted by Pyruvate Dehydrogenase (PDH) into Acetyl-Coenzyme A, recondensed to citrate, which then supports the Krebs cycle. These activities linked to citrate place CIC at a nodal point in regulation of mitochondrial activity and metabolism.

Citrate, which is produced predominantly in the mitochondria via glucose-derived pyruvate, serves as a key substrate for the generation of energy and as an allosteric modulator of several enzymes as well. In the mitochondria, citrate is oxidized via the Krebs cycle and Oxidative Phosphorylation (OXOPHOS), while in the cytoplasm it supports lipid synthesis and blunts glycolysis by inhibiting phosphofructokinase-1 (PFK1). Additionally, the entry of malate into the mitochondria in exchange for citrate stimulates OXOPHOS and is coupled to the transport of one proton. This modality of exchange maintains both electroneutrality across the mitochondrial membrane and OXOPHOS, because malate enters into the Krebs cycle in place of citrate.

The majority of tumor cells display alterations in metabolism relative to normal cells that are intimately connected with cancer development, progression, and invasiveness. These metabolic changes center in large part upon the different utilization of citrate compared to normal cells.

Mitochondrial DNA mutations, the hypoxic and nutrient restricted microenvironment, as well as oncogenic mutations that reduce the activity of mitochondrial enzymes, all contribute to oxidative and respiration stress endured by these organelles. Consequently, cancer cells produce radical oxygen species (ROS), which increase oxidative burden, but also work to the advantage of tumors because low ROS levels produced by the stroma or within cancer cells promote proliferation. This oxidative instability is at the same time also a double edge sword and a vulnerable aspect of cancer cells, given that enhancing ROS production leads to tumor killing and to activation of a specialized form of autophagy, termed mitophagy. Although activation of mitophagy in the adjacent stroma feeds cancer cells with nutrients required for proliferation, avoidance of mitophagy within the tumor appears instead to be advantageous to cancer growth at least in some conditions.

Methods

Cells, Reagents, Antibodies, Primers.

Cells were grown in Dulbecco's modified Eagle's medium (DMEM, 5 mM glucose, with glutamine and pyruvate from Invitrogen; Carlsbad, Calif.) and supplemented with 10% fetal calf serum (FCS). Early passage cell lines or frozen pellets were used for screening of CIC expression levels (FIG. 1A). All the reagents for the study of complex I activity were purchased from Sigma-Aldrich (St. Louis, Mo.). The CIC specific shRNA vectors were purchased from Origene Technologies (Rockville, Md.). The vectors expressing human CIC untagged or Flag-Myc epitope tagged were also from Origene. The anti-CIC antibody was obtained from Santa Cruz Biotech (Santa Cruz, Calif.), employed at 1:1000 dilution in immuno-blot and at 1:100 in immuno-fluorescence; the anti-mHsp70 and anti-mitofilin antibody were from Novus Biological (Littleton, Colo.) employed at 1:500 in immuno-fluorescence and 1:1000 in immuno-blot; for the LC3 immuno-blot, a mixture of two antibodies was used each at 1:1000 dilution (Novus Biological). The LAMP-1 antibody was from Abcam (Cambridge, UK). The sequences of primers used were: the human cytochome c oxidase: forward: 5'-TCGCCGAC-CGTTGACTATTCTCT-3' (SEQ. ID NO: 1); Reverse:5' AAGATTATTACAAATGCATGGGC-3' (SEQ. ID NO: 2). The zebrafish NADH-dehydrogenase: forward: 5'-AGGGT-TGCTGGGATGGCAGAGCTCGGTA-3' (SEQ. ID NO: 3); reverse:5' CACTCCATCAAAGTGACCCCTTAGCAT-3' (SEQ. ID NO: 4). The zebrafish p53: forward: 5'-ACATGA AATTGCCAGAGTATGTGTC-3' (SEQ. ID NO: 5); Reverse: 5' TCGGATAGCCTAGTGCGAGC 3' (SEQ. ID NO: 6).

Strategy for the Generation of CIC Wild-Type and CIC Mutant Expressing Vectors, and of Stable Cell Lines.

The two cDNA clones expressing human untagged CIC and epitope tagged CIC were cloned into the pcDNA4/TO tetracycline regulated vector (Santa Cruz Biotech, T-Rex system). Stable tetracycline inducible cell lines were obtained.

Quantification of Metabolites, ATP, Oxygen, ROS, MMP and Mitochondrial Mass.

The concentration of citrate, lactate, isocitrate, and malate were assessed using specific kits from BioVision (Milpitas, Calif.). Cellular ATP levels were determined via the ATP kit (Promega; Fitchburg, Wis.), while oxygen consumption rates were measured using the BD oxygen biosensor systems (OBS) from BD Bioscience (Franklin Lakes, N.J.). Triplicate samples of 50,000 cells were seeded onto 96-well OBS plates. The number of cells was determined at each time point by sampling cells seeded into side-by-side plates. Fluorescence was measured from the bottom of the well every 24 h and measurements were normalized by subtracting the reading from the same well prior to the addition of the cells (blank). For measurement of reactive oxygen species (ROS), H2DCFDA was used (Invitrogen). Mitochondrial mass was assessed by using mitotracker green (Invitrogen), as per manufacturer instructions, or nonyl acridine orange at a final concentration of 300 nM, followed by analysis by flow cytometry. Mitochondrial membrane potential (MMP) was studied with the JC1 assay kit from Cayman Chemical (Ann Arbor, Mich.).

Mice and Tumors.

To produce tumor xenografts, $5 \times 10^6$ cells were resuspended in PBS and injected subcutaneously in the flanks of female nude mice. For drug treatments, mice were randomized to receive either PBS or a PBS solution of BTA at a concentration 26 mg/kg which was administered via intraperitoneal route three times a week. Mice were pre-treated twice prior to the inoculation of tumor cell lines. Once detectable tumors started to form, their size was measured with a caliper in three dimensions. Serial measurements were made at two-three day intervals after the identification of the initial cellular mass to determine growth curves in vivo. Tumor volume was calculated using the formula for a prolate spheroid: volume=$(4/3) \times a^2 b$, where a is the width and b is the length. All animals were sacrificed when the tumors exceeded 1.5 cm. At the completion of experiments, tumors were excised, weighed and statistical significance of differences in tumor volume were made using two factor repeated measures analysis of variance followed by Fisher's last significant difference test for multiple comparisons. The trial administration of BTA to explore its toxic effects, was conducted on 8 non immuno-compromised mice, randomized in two groups, and injected for five consecutive months. Animals were monitored once a week for the presence of signs of disease, particularly neurological disturbances or weight loss, and they were weighted periodically.

Statistical Analysis.

Data are expressed as means±standard deviations (SD). The two-tailed Student t test was used for all statistical analysis of experiments presented and Excel was used for statistical calculations. Significant differences are indicated using the standard Michelin Guide scale ($P<0.05$, significant; $P<0.01$, highly significant; $P<0.001$, extremely significant).

Results

CIC Levels are Elevated in Human Cancers and its Activity is Required for Tumor Proliferation In Vitro.

The transcription rate of the CIC promoter is enhanced by several oncogenic pathways including mutant forms of p53 and Myc, while it is repressed by the tumor suppressor PTEN. CIC mRNA levels are elevated in various cancer cell lines and human tumors correlating with poor survival rates or with the development of metastatic disease (FIG. 1BC). For FIG. 1B, data were obtained from the Oncomine database (Compendia Bioscience; Ann Arbor, Mich.) by selecting a minimal threshold p-value of 0.0005. In FIG. 1C, N indicates the total number of patients. In one study conducted, 69 patients with elevated CIC levels were dead after 5 years, versus 158 patients with lower levels, who were still alive. In a second study, 18 patients with elevated CIC levels developed metastasis after 5 years, versus 6 with lower CIC levels who remained metastasis free. p values are indicated in each panel. CIC levels were found elevated in many, but not all of the tumor cell lines derived from the NCI50 panel. CIC is almost undetectable in a model system of ductal non-invasive carcinoma in situ (DCIS) or in pseudo-normal MCF10A mammary cells, compared to invasive MCF10A cells expressing the Ras/Erb B oncogenes, or to MDA-MB-231 and BT549 cell lines (FIG. 1D). These observations suggested that CIC expression correlates with aggressiveness. FIGS. 1E and 1F show clonogenic assays performed in MBA-MD-231 cells. Cells were transfected with control shRNA vector (indicated as ct), or with vectors harboring three CIC shRNA (shRNA 1, 2, 3), each harboring a puromycin resistance gene. Vectors were transfected individually (panel E) or in different combinations (panel F) and proliferation was assessed after one week of antibiotic selection. Representative CIC expression levels relatively to actin levels are shown in panel E (bottom panel), and representative plates derived from the combination transfection experiments are shown at the bottom of panel F. In MBA-MD-231 cells, expression of three different CIC shRNAs, each transfected individually, resulted in a small reduction in CIC protein and in a modest growth inhibition (FIG. 1E). However, co-transfection of combination shRNAs completely blunted proliferation (FIG. 1F) and clones that survived these experiments again displayed CIC levels nearly similar to control. Thus, complete CIC inhibition is incompatible with survival of MBA-MD-231 cells.

Figure 2:
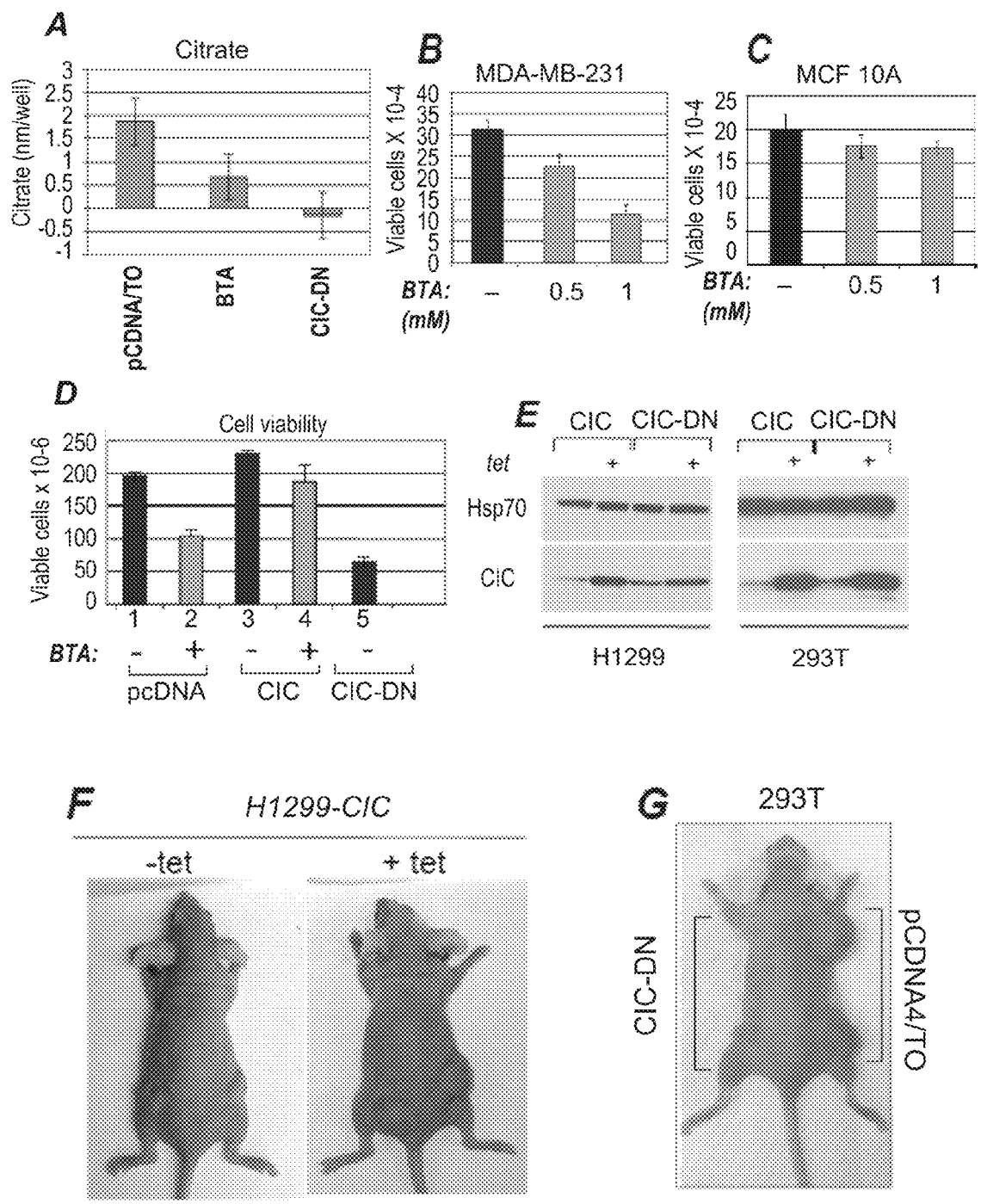
FIG. 2 shows that CIC maintains the intracellular pool of citrate and promotes proliferation. Panel A shows citrate levels in cells expressing endogenous CIC (nM/well) were assessed in 293T cell lines harboring the pcDNA/TO vector and treated with either DMSO or with 1 mM BTA, or in cells expressing CIC-DN. Negative values are due to subtraction of background rates. Panels B and C show the dose dependent growth inhibition of BTA in MDA-MB-231 or MCF10A cells. Panel D shows control H1299 cells (pcDNA/TO), or cells expressing the CIC proteins indicated at the bottom of each panel, were treated with DMSO (−), or with 1 mM BTA (+). Cell viability was assessed with trypan blue exclusion. Panel E shows expression of CIC or CIC-DN in tetracycline inducible stable clones of H1299 or 293T cells, in presence or absence of tetracycline. Panel F shows female athymic balbc/nude mice injected with H1299 cells expressing inducible CIC in the presence or absence of tetracycline or of vehicle control provided in the water. Panel G shows 293T cells stably transfected with the control vector (pCDNA4/TO), or expressing inducible CIC-DN were injected in the right and left flanks of female athymic mice, respectively.

To specifically probe the relevance of the citrate export activity of CIC on proliferation, a non-cleavable benzenetricarboxylate analog (BTA; Compound I) that suppresses CIC-dependent transport of citrate in vivo was used. A CIC mutant protein was designed where three amino acid residues necessary for citrate export, K190, N194 and R198, were replaced with C190, I194 and C198, respectively. The CIC-DN mutant did not affect mitochondrial localization or embedding in the mitochondrial membrane (FIG. 1G) but exhibited dominant negative activities, as judged by its ability to lower the concentration of citrate in cells expressing endogenous CIC (FIG. 2A). In Panel 2A, citrate levels in cells expressing endogenous CIC (nM/well) were assessed in 293T cell lines harboring the pcDNA/TO vector and treated with either DMSO or with 1 mM BTA, or in cells expressing CIC-DN. Negative values are due to subtraction of background rates. Limited tryptic digestion experiments further showed an impaired ability of CIC-DN to interact with the citrate analog BTA. To assess the effects of CIC and of its inhibition on cell growth, several cell lines were treated with BTA or were transfected with the vectors encoding CIC or CIC-DN. In MBA-MD-231, but not in the pseudo-normal MCF10A cells, treatment with BTA decreased proliferation rates in a dose-dependent manner (FIG. 2BC). Such differential effects suggested a preferential sensitivity of tumor cells to CIC inhibition, a view supported by studies shown later. Furthermore, over-expression of wild-type CIC modestly but reproducibly enhanced the proliferation potential of H1299 cells, and rescued growth inhibition due to BTA treatment (FIG. 2D, compare lane 2 with lane 4). By contrast, expression of CIC-DN was detrimental for cell growth (FIG. 2D, lane 5).

These results provide the first line of evidence that inhibition of CIC hampers cancer cell proliferation, show that CIC is a target of the anti-proliferative action of BTA in vivo, and demonstrate the importance of the citrate export pathway activity of CIC in regulation of growth.

Inhibition of CIC Inhibits Tumorigenesis In Vivo, but is Non-Toxic to Adult Normal Tissues.

Figure 3:
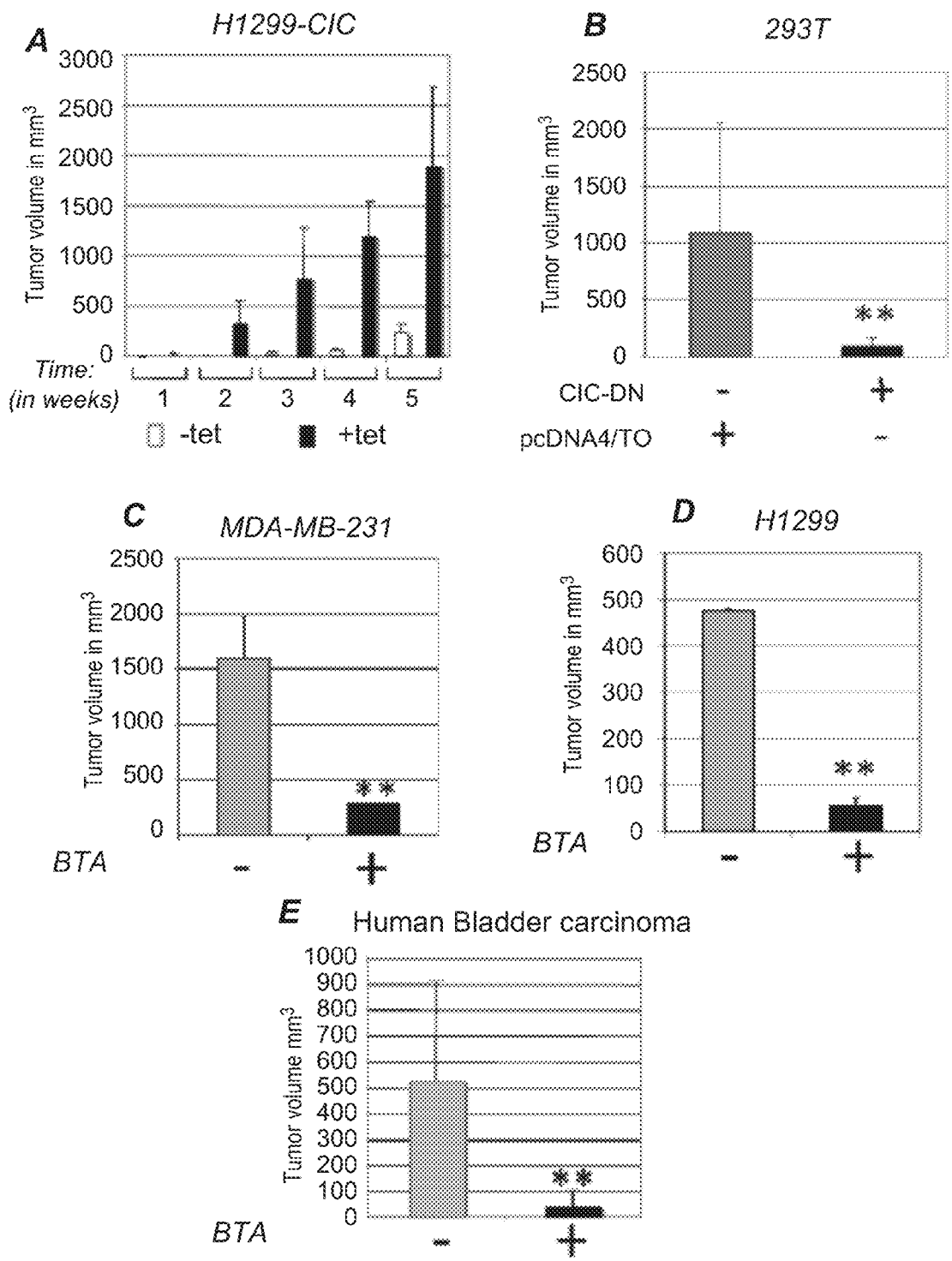
FIG. 3 shows that CIC is rate-limiting for tumorigenesis in vivo. Panel A shows Female athymic balbc/nude mice injected with H1299 cells expressing inducible CIC in the presence or absence of tetracycline or of vehicle control as described in FIG. 2F and tumor volumes were assessed several weeks after implantation. White bars indicate control group, while black bars show tumor growth in cells expressing CIC. Panel B shows tumor volumes assessed after implantation in nude mice of T293 cells expressing control vector (pCDNA/TO) or dominant negative CIC (CIC-DN). Panels C-E show tumor volumes in female athymic balbc/nude mice injected with breast cancer MDA-MB-231 cells (C); with lung cancer H1299 cell lines (D) cells; or with bladder cancer cells derived from T24 cells (E). Tumor volumes derived from mock treated (−) and BTA treated (+)

To explore whether CIC affects tumor development in vivo, stable lung cancer (H1299) and SV40 T-antigen transformed embryonic kidney (293T) cell lines expressing tetracycline inducible CIC or CIC-DN were generated (FIG. 2E). Their growth capacity after implantation in immuno-deficient mice was assessed. CIC dramatically accelerated the onset and size of tumors, while CIC-DN led to a reduction of growth (FIG. 2FG, and FIG. 3AB). CIC proteins were detectable in these tumors. Similarly to CIC-DN, BTA also exhibited anti-cancer activity in various tumor types, including in aggressive breast cancer cell lines MDA-MB-231, lung cancer cells H1299 as well as in bladder cancers cell lines (FIG. 3CE). The anti-tumor effect of BTA observed in MDA-MB-231 cells as a single agent (FIG. 3C), is of particular relevance given that these cells are representative of triple receptor negative breast tumors that are often hormone- and chemo-resistant. During the course of these experiments, BTA-treated mice showed no evidence of illness or toxicity. Therefore, potential side effects of this compound in non immuno-compromised animals were examined Mice were randomized and BTA was administered twice a week for five consecutive months. There was a small but statistically significant reduction of the body weight in all of the BTA-treated animals, but animals could be treated for a long period of time without showing any evidence of toxicity. Thus, inhibition of CIC activity is non-toxic in the adult normal mouse. By contrast, CIC is rate limiting for tumor progression in vivo, and its inhibition has therapeutic potential.

CIC Inhibition Leads to Mitochondrial Dysfunction, Destabilizes MMP and Enhances Glycolysis.

The molecular mechanisms by which CIC affects proliferation were examined. The function of CIC has been primarily linked to glucose-derived fatty acid (FA) synthesis, because of its role in citrate export. Therefore, the metabolism of D-[1,6-$^{13}C_2$] glucose via NMR mass spectrometry was studied. In support of the proposed role of CIC in promoting de novo lipogenesis, both BTA and CIC-DN severely reduced the ability of cells to convert glucose into FA. However, the total FA levels, which can be synthesized also from glycerol and amino acids, were modestly reduced at 16 hours after BTA treatment, but at later time points they were increased. Furthermore, incubation of BTA-treated cells with the lipid precursor, palmitic acid was not sufficient to rescue proliferation. Thus, depletion of lipids unlikely represents the only mechanism by which CIC inhibition affects tumor growth.

Since CIC is a mitochondrial protein, the mitochondrial morphology was examined Immuno-fluorescence experiments showed that in CIC-expressing cells the mitochondria were highly interconnected, while in cells harboring CIC-DN the mitochondrial network was dispersed with fewer and fragmented mitochondria (FIG. 4A, indicated by arrow; compare panel 3 with panels 1 and 2). Mitochondria structure is a direct reflection of metabolic state, and a fragmented phenotype has often been observed in conditions of reduced OXOPHOS and of enhanced glycolysis, as well as a consequence of ROS production. Thus, CIC influences mitochondrial activity and glucose metabolism. BTA enhanced the levels of glucose-derived lactate, and the total levels of lactate were elevated in cells where CIC was inhibited (FIG. 4B). In the case of CIC-DN, lactate was more prominently increased in the media than inside the cells, demonstrating that this mutant and BTA are not exactly identical in the way they increase glucose flux (FIG. 4B). Consistent with a protective role of CIC on mitochondria activity and OXOPHOS, its inhibition led to a decline of respiratory Complex-I activity (FIG. 4C). This was accompanied by a loss of mitochondrial membrane polarity (FIG. 4D) and by the production of ROS, which was rescued by the general ROS m scavenger, N-acetyl-cysteine (NAC) (FIG. 4E).

The collapse of MMP indicated that CIC dysfunction perturbs the proton gradient, which is directly linked to the exchange between citrate and malate promoted by CIC, as well as the flux of anaplerotic substrates across the mitochondrial membrane. Specifically, the depletion of citrate induced by CIC inhibition would predictably lower the levels of malate and isocitrate, which are produced via citrate oxidation and isomerization, respectively. Further, the shift of metabolism towards glycolysis due to blocking of CIC activity may consume pyruvate in the cytoplasm for lactate production, thus rendering pyruvate less available for mitochondrial metabolism. Pyruvate, citrate, and isocitrate can all enter the Krebs cycle at various steps generating reducing equivalents for the electron transport chain, which in turn stabilize MMP. The levels of several anaplerotic substrates in cells where CIC was inhibited were measured. The levels of malate and isocitrate were reduced (FIG. 4FG), and addition to the media of pyruvate, in the form of the membrane permeable methyl-pyruvate, partially restored mitochondrial membrane polarity, as well as complex I activity. Methyl-pyruvate and NAC also partially prevented loss of viability in cells treated with BTA (FIG. 5A). Thus, CIC preserves mitochondrial activity at least in part by maintaining adequate levels and flux of anaplerotic substrates, which in turn prevent depolarization of the mitochondrial membrane, while its inhibition leads to mitochondrial dysfunction. Impairment of CIC activity also re-wires the metabolism towards glycolysis, either as a consequence of mitochondrial dysfunction (the Warburg effect) or due to the lowered concentration of citrate that enhances PFK1 activity (see scheme in FIG. 1A).

The Ability of CIC to Restrain the Glycolytic Addiction of Tumor Cells Leads to a Growth Advantage.

The above data indicated that CIC inhibition exacerbates the Warburg effect, a metabolic trait that is proposed to promote malignancy. Glycolysis is metabolically advantageous when glucose is abundant, because in these conditions it can generate ATP at faster rates compared to OXHOPHOS. By contrast, rapidly growing tumors surpass the ability of the microenvironment to provide nutrients, and switch towards alternative metabolic pathways, including OXHOPHOS, for energy production. Thus, CIC can be important for adaptation when glucose is limiting. Likely due to the enhanced glycolytic behavior, at high concentrations of glucose (25 mM) oxygen consumption rates and ATP levels were not significantly modified in cells where CIC was inhibited compared to control cells. However, at lower, yet physiological glucose levels (5 mM), cells expressing CIC consumed more oxygen and produced more ATP relatively to BTA-treated or CIC-DN-expressing cells (FIG. 5BC). Cell cycle analysis further revealed that glucose restriction led to induction of apoptosis in BTA treated cells, while expression of CIC, but not of CIC-DN was protective in these conditions (FIG. 5D). Collectively, therefore, these results provide for a model whereby CIC restrains the excessive reliance upon glycolysis allowing tumor cells to shift towards OXPHOS for ATP production, ultimately favoring survival when glucose is limiting.

CIC is Induced by Mitochondrial Respiration Injury and Prevents Mitochondrial Depolarization and Depletion.

The mitochondria of tumor cells undergo oxidative stress due to mtDNA and to oncogenic mutations that affect the activity of mitochondrial enzymes involved in respiration. Mitochondrial damage in turn triggers quality control systems consisting of mitochondria degradation via autophagy/mitophagy. Thus, CIC can exert a protective role on mitochondrial damage and disposal. First, immuno-fluorescence and cellular sub-fractionation experiments demonstrated recruitment of the autophagic machinery in the form of the active-lipidated form of LC3 and of lysosomes, to the mitochondria of cells expressing CIC-DN or treated with BTA, but not in CIC containing cells (FIG. 5E, compare panels 2 and 5; FIG. 5F, compare lanes 6 and 8 with lanes 2 and 4; Figure S6AB). Furthermore, kinetic studies where mitochondrial content was assessed with the marker of mitochondrial mass, mitofilin, showed a reduction of mitochondrial quantity as a function of time, following BTA treatment or CIC-DN induction (FIG. 5G, compare lanes 2 and 3, and lanes 5 and 6 with lanes 1 and 4, respectively). This mitochondrial depletion coincided with activation of autophagy, as judged based on LC3 activation and conversion (FIG. 5G, lower panel). Similar results were obtained when mitochondrial amount was studied with a second marker of mitochondrial content, namely Nonyl-Acridine Orange (NOA) (FIG. 6A, compare lanes 2 and 3 with lane 1). Blocking of autophagy with 3-Methyladenine (3MA) restored mitochondrial amount (FIG. 6A, compare lanes 5 and 6 with lanes 2 and 3), thus suggesting clearance of these mitochondria by mitophagy/autophagy. 3MA also prevented cell death induced by BTA in glucose-restricted conditions.

Autophagy can be organelle selective or proceed as a bulk degradation process of multiple cellular compartments. CIC did not interfere with global autophagic flux in response to the mTOR inhibitor, rapamycin, or to glucose restriction, suggesting that it might specifically affect mitophagy (Figure S6D). The mitochondrial respiration uncoupler carbonyl-cyanide-3-chlorophenylhydrazone, CCCP, which induces depolarization of the mitochondrial membrane and mitochondria fragmentation followed by mitophagy was employed. Cells where CIC was abundant were protected from MMP loss induced by CCCP, while expression of CIC-DN destabilized MMP independently of CCCP and failed to restore mitochondrial membrane polarity (FIG. 6B, compare lanes 3 and 4 with lanes 1 and 2; and lane 6 with lane 4, respectively). Furthermore, in conditions in which CCCP was washed out from the media after treatment, H1299 and CIC-expressing cells maintained stable mitofilin content (FIG. 6C, compare lanes 4 and 5 with lanes 1 and 2; quantified in FIG. 6D) as well as normal mitochondrial structure and morphology (FIG. 6E). The protection seen in naïve H1299 cells correlated with an induction of the expression levels of endogenous CIC by CCCP (FIG. 6C, compare lane 1 versus lane 4 in the CIC immuno-blot). Other types of mitochondrial stressors, such as rotenone, also induced CIC expression levels.

These results indicate that CIC is a sensor and an effector of mitochondrial stress. Via its citrate export ability, CIC stabilizes membrane potential minimizing mitochondrial depletion. By contrast, cells where CIC is inhibited trigger autophagic clearance of mitochondria.

The Knock-Down of the CIC Orthologous Gene in Zebrafish Induces Mitochondrial Loss and Activation of Autophagy.

Genes that promote tumorigenesis are often necessary for embryonic development, and some of these genes are metabolic modulators, given that embryogenesis and tumorigenesis are energetically demanding. Additionally, whether changes of CIC dosage affect embryogenesis in the model organism zebrafish was investigated. This approach was possible because human and zebrafish CIC proteins display a high degree of homology. By using a morpholino-based (MO) knock-down strategy, it was found that the CIC MO led to a stark dose-dependent phenotype, and produced a relatively small percentage of dead embryos (34%, FIG. 7A, FIG. 7E). At 24 hours post-fertilization, the head was flattened and reduced along the ventral-dorsal axis and at later steps of development CIC morphants displayed a prominent reduction of the entire cranial region, involving the size of the brain and the jaw. The heart was small and surrounded by pericardial edema, indicative of cardiac dysfunction (FIG. 7B). Confirming the efficiency of the knockdown, a progressive decline of the expression levels of CIC was seen with increasing doses of MO, paralleled by a reduction in the levels of mitofilin and of mitochondrial, but not nuclear DNA (FIG. 7C and FIG. 7D, respectively). Similar to what observed in human tumor cells, LC3 total levels and the conversion to the lipidated form were starkly increased (FIG. 7C, compare lanes 2 to 4 with lane 1 in the LC3 immunoblot), and the phenotypes of the CIC-MO were largely rescued by 3MA (FIG. 7D). CIC morphants recapitulated features of VCFS, which is characterized by multiple abnormalities including cardiac defects, facial and jaw anomalies and cleft palate.

The diagram in FIG. 8 summarizes the findings. The mitochondria of tumor cells endure oxidative and respiration stress caused by the nutrient restricted microenvironment, by oncogenic activation, and by altered activity of mitochondrial enzymes. High CIC levels in tumors allow for adaptation to nutritional stress and resistance to mitochondria respiration injury. This protective effect of CIC on the tumor mitochondria relies upon an inhibition of glycolysis, promotion of mitochondrial OXOPHOS and ATP production, and stabilization of the mitochondrial membrane potential (MMP). These activities of CIC have been mechanistically linked herein to its ability to promote the export of citrate and to maintain adequate levels and flux of other anaplerotic substrates. By contrast, genetic or pharmacologic inhibition of CIC increases ROS levels, compromises respiratory capacity and leads to mitochondrial dysfunction and depletion via autophagy, preventing adaptation to oxidative or respiration stress, and ultimately leading to tumor killing.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated.

What is claimed is:

1. A method of treating a neurodegenerative disorder in a subject, comprising:
administering to the subject an effective amount of a compound of the following structure:

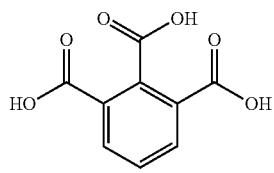 [SMILES: O=C(O)c1cccc(C(=O)O)c1C(=O)O]

or a hydrate or pharmaceutically acceptable salt thereof, wherein the neurodegenerative disorder is Parkinson's disease.

2. The method of claim 1, further comprising administering a second therapeutic agent to the subject.

3. The method of claim 2, wherein the second therapeutic agent is selected from the group consisting of levadopa, a dopamine agonist, an anticholinergic agent, a monoamine oxidase inhibitor, a COMT inhibitor, amantadine, rivastigmine, an NMDA antagonist, a cholinesterase inhibitor, riluzole, an anti-psychotic agent, an antidepressant, and tetrabenazine.

* * * * *

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
tcgccgaccg ttgactattc tct                                          23

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
aagattatta caaatgcatg ggc                                          23

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
agggttgctg ggatggcaga gctcggta                                     28

<210> SEQ ID NO 4
<211> LENGTH: 27
<212> TYPE: DNA
<213> ORGANISM: Artificial Sequence
<220> FEATURE:
<223> OTHER INFORMATION: Primer
```

```
<400> SEQUENCE: 4
cactccatca aagtgacccc ttagcat                                               27

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
acatgaaatt gccagagtat gtgtc                                                 25

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tcggatagcc tagtgcgagc                                                       20
```